United States Patent [19]
Faust et al.

[11] Patent Number: 6,059,753
[45] Date of Patent: May 9, 2000

[54] REUSABLE CASSETTE HOUSINGS AND METHODS

[75] Inventors: Mark Henry Faust, Lino Lakes; Jay Gregory Johnson, Maple Plain, both of Minn.

[73] Assignee: SIMS Deltec, Inc., St. Paul, Minn.

[21] Appl. No.: 09/086,186

[22] Filed: May 28, 1998

Related U.S. Application Data

[62] Division of application No. 08/696,794, Aug. 14, 1996, Pat. No. 5,788,671.

[51] Int. Cl.$^7$ .................................................. A61M 37/00
[52] U.S. Cl. .......................... 604/131; 604/500; 604/508
[58] Field of Search .................... 604/131, 151, 604/153, 500, 503, 507, 508

[56] References Cited

U.S. PATENT DOCUMENTS

| | | |
|---|---|---|
| 3,402,673 | 9/1968 | Ballentine et al. . |
| 3,559,644 | 2/1971 | Stoft et al. . |
| 3,620,650 | 11/1971 | Shaw . |
| 4,187,057 | 2/1980 | Xanthopoulos . |
| 4,236,880 | 12/1980 | Archibald . |
| 4,482,347 | 11/1984 | Borsanyi . |
| 4,559,038 | 12/1985 | Berg et al. . |
| 4,565,542 | 1/1986 | Berg . |
| 4,585,399 | 4/1986 | Baier . |
| 4,650,469 | 3/1987 | Berg et al. . |
| 4,657,486 | 4/1987 | Stempfle et al. . |
| 4,671,792 | 6/1987 | Borsanyi . |
| 4,678,011 | 7/1987 | Weber . |
| 5,017,059 | 5/1991 | Davis . |
| 5,074,756 | 12/1991 | Davis . |
| 5,078,683 | 1/1992 | Sancoff et al. . |
| 5,165,874 | 11/1992 | Sancoff et al. . |
| 5,213,483 | 5/1993 | Flaherty et al. . |
| 5,226,886 | 7/1993 | Skakoon et al. . |

(List continued on next page.)

FOREIGN PATENT DOCUMENTS

| | | |
|---|---|---|
| WO 93/10853 | 6/1993 | WIPO . |
| WO 96/27402 | 9/1996 | WIPO . |
| WO 97/02059 | 1/1997 | WIPO . |

OTHER PUBLICATIONS

Block Medical, Inc. literature for Verifuse System, 1 page, dated Nov. 1990.
Medfusion, Inc. Operations Manual for Medfusion WALK-MAN™ Ambulatory Infusion Pump, 92 pages, dated Apr., 1990.
Medex Ambulatory Infusion Systems literature, entitled "WalkMed Pump Disposable Products," 2 pages, dated 1992.
Medex Ambulatory Infusion Systems literature, entitled "WalkMed PCA," 2 pages, dated 1993.
Bard Ambulatory PCA Pump literature, 2 pages, dated Jun. 1990.
Bard MedSystem Division, C.R. Bard, Inc., Quick Reference Guide, 2 pages, dated Feb. 1992.
Bard MedSystems Division, C.R. Bard, Inc., Bard® Ambulatory PCA Pump Operator's Manual, 43 pages, Apr. 1990.
AVI, Inc. literature entitled "The AVI Advantage,", 2 pages, dated 1983.
AVI, Inc. literature, entitled "Bridging the Gap," 6 pages, dated Apr. 22, 1983.
Abbott Laboratories Hospital Products Division literature, entitled "The Blue Line System LifeCare®," 16 pages, dated Jul., 1990.
Abbott Laboratories Hospital Products Division literature, entitled "LifeCare® Electronic Flow Control Systems Catalog," 34 pages, dated May, 1985.

*Primary Examiner*—John D. Yasko
*Attorney, Agent, or Firm*—Merchant & Gould P.C.

[57] ABSTRACT

Reusable cassettes for a drug pump are disclosed to house a fluid reservoir and tubing extending from the reservoir across a tubing support surface of the pressure plate of the cassette. A hinged housing provides reversible access to the fluid reservoir. Reuse of a portion of the pressure plate is also disclosed.

9 Claims, 5 Drawing Sheets

U.S. PATENT DOCUMENTS

| | | |
|---|---|---|
| 5,330,431 | 7/1994 | Herskowitz . |
| 5,336,190 | 8/1994 | Moss et al. . |
| 5,397,222 | 3/1995 | Moss et al. . |
| 5,425,173 | 6/1995 | Moss et al. . |
| 5,441,163 | 8/1995 | Carrasco . |
| 5,482,446 | 1/1996 | Williamson et al. . |
| 5,509,901 | 4/1996 | Milijasevic . |
| 5,531,697 | 7/1996 | Olsen et al. . |
| 5,540,561 | 7/1996 | Johnson . |
| 5,564,915 | 10/1996 | Johnson . |
| 5,567,119 | 10/1996 | Johnson . |
| 5,632,394 | 5/1997 | Mecca et al. . |

REUSABLE CASSETTE HOUSINGS AND METHODS

This application is a Divisional of application Ser. No. 08/696,794, filed Aug. 14, 1996, now U.S. Pat. No. 5,788,671 which application(s) are incorporated herein by reference.

FIELD OF THE INVENTION

The present invention relates to medical devices including infusion systems and infusion pumps for delivering fluid to a patient. In particular, this invention relates to reusable cassettes and pressure plates.

BACKGROUND OF THE INVENTION

In medical applications, it is sometimes necessary to deliver fluid intravenously to a patient undergoing treatment. The fluid may be contained in a bag or other fluid reservoir, conveyed through a tube, and inserted into the patient's vein. At times, the amount of fluid conveyed to the patient must be controlled or regulated. In those instances where the fluid to the patient must be controlled, pumps have been used.

One pump is described in U.S. Pat. No. 4,559,038. This pump controls the delivery of fluid from the reservoir to the patient. In the '038 patent, the fluid is in a bag held in a container, or cassette, immediately adjacent to the pump. The pump controls the amount of fluid to the patient by physically pressuring the tube from the bag to the patient, and restricting the volume of fluid allowed to flow to the patient. The pump includes a pump mechanism which engages the tube and squeezes the tube against a pressure plate of the cassette to effect pumping of fluid.

It is also known to use the pump with a fluid reservoir that is remote, or separate from the pump. Typically, in a remote system, the fluid is contained in a bag and hung on a device separate from the pump. The bag has a tube extending from the bag, across a section of the pump, and then to the patient. Again, the pump controls the amount of fluid to the patient by mechanical pressure on the tube. A pressure plate mounted to the pump allows the pump mechanism to engage the tube to effect pumping.

In the past, certain types of pressure plates have been used to connect the pump to the tube. Because of reasons such as safety and cleanliness, the pressure plate is permanently attached to the tube. When the fluid reservoir is empty, or the treatment to the patient completed, the tube and pressure plate are thrown away. Disposing of the pressure plate contributes to waste and expense. There is a need for systems and methods that allow reuse of the pressure plate. In the case of cassettes enclosing the fluid reservoir, the cassette and the reservoir are discarded along with the pressure plate portion and the tube. There is a need for systems and methods that allow reuse of the cassette.

SUMMARY OF THE INVENTION

The present invention relates to reusable cassettes and methods of using cassettes having a hinged construction to allow selective access to an interior for removal and replacement of a used fluid reservoir. The cassettes may also preferably include a slot in a tubing support portion to allow a tube to be positioned through the tubing support portion without having to thread the tube through an anchor of the tubing support portion. The present invention also relates to pressure plates and methods for reuse of the pressure plate or a portion of the pressure plate.

One aspect of the present invention relates to a reusable cassette mountable to a pumping mechanism for positioning a tube adjacent to a plurality of tube engaging members of the pumping mechanism. The cassette includes a tubing support surface having a pump anchor and two hooks. The tubing support surface is separable into a first support surface portion and a second support surface position. The cassette further includes a housing having a top edge, a bottom, a front face, a back face and two side faces. The housing is permanently affixed to at least a portion of the tubing support surface and sized for housing a fluid reservoir. A hinge is provided to reversibly open and close the housing. The hinge is positioned at a bottom corner of the housing, wherein the housing opens and closes along hinge separation lines which traverse at least a portion of the front face and the back face extending from the top edge to the hinge along each face and along the junction between the first support surface portion and the second support surface portion on the tubing support surface.

Another aspect of the present invention relates to a reusable cassette mountable to a pumping mechanism for positioning a tube adjacent to a plurality of tube engaging members of a pumping mechanism. The cassette includes a tubing support surface having a pump anchor and two hooks. The cassette further includes a housing having a bottom face, a front face, a back face and two side faces, wherein the housing is affixed to the tubing support surface and is sized for housing a fluid reservoir. A hinge is provided to reversibly rotate one rotatable face of the housing relative to the remainder of the housing, wherein rotation of the one rotatable face of the housing provides access to the fluid reservoir. The hinge defines an axis of rotation extending generally transverse to the one rotatable face. The tubing support surface may be slotted to allow for positioning of the tube through the tubing support surface. This construction allows for reuse of the pressure plate without threading the tube through a hole in the tubing support surface. A support is preferably positioned to support the rotatable face in the closed position. The support prevents further rotation of the face past the closed position, and the support prevents the face from being able to be pried open.

A further aspect of the present invention relates to a reusable cassette mountable to a pumping mechanism for positioning a tube adjacent to a plurality of tube engaging members of the pumping mechanism. The cassette includes a housing sized to hold a fluid reservoir, the housing having a bottom face, a front face, a back face and two side faces. A pressure plate with a tubing support surface is mountable to the housing and has an anchor and two hooks. A hinge extends along the bottom face of the housing to separate the housing into a front half and a back half to reversibly open and close the housing to access the interior of the housing. A snap holds the front half to the back half in a closed position. Structure is provided for retaining the pressure plate with the front half and the back half of the housing in the closed position. One structure for retaining the pressure plate with the housing includes a post and hole arrangement between the housing and the pressure plate. Another structure for retaining the pressure plate with the housing includes a permanent mount between one of the halves of the housing and the pressure plate. The tubing support surface may be slotted to allow for positioning of the tube through the tubing support surface. This construction allows for reuse of the pressure plate without threading the tube through a hole in the tubing support surface.

Another aspect of the present invention relates to a pressure plate mountable to a pumping mechanism for positioning a tube adjacent to a plurality of tube engaging members of the pumping mechanism. The pressure plate includes a reusable body having first and second ends, an anchor at the first end, and two hooks at the second end. The body defines a recess between the first and second ends. A separate insert having a tube supporting surface is positioned in the recess of the body. The anchor and the hooks are mountable to the pumping mechanism to position the tube between the tube supporting surface of the insert and the tube engaging members of the pumping mechanism. The insert includes a plurality of spaced apart rib pairs sized to receive the tube. The anchor may have a closed loop shape or an open hook shape. In the case of a closed loop shape, the body may include a slot extending from an edge of the body through the body and located between the hooks and the anchor. Retention tabs may be provided for holding the insert to the body.

The present invention also relates to methods of using cassettes and pressure plates wherein the housing, the pressure plate, and/or a portion of the pressure plate may be reused.

DETAILED DESCRIPTION OF THE PREFERRED EMBODIMENTS

The reusable cassettes of this invention are configured to permit ready access to a fluid reservoir and tube. Reuse of the pressure plate or a portion of the pressure plate is possible whether the pressure plate is part of a self-contained fluid reservoir cassette or a remote fluid reservoir system.

Figure 1:
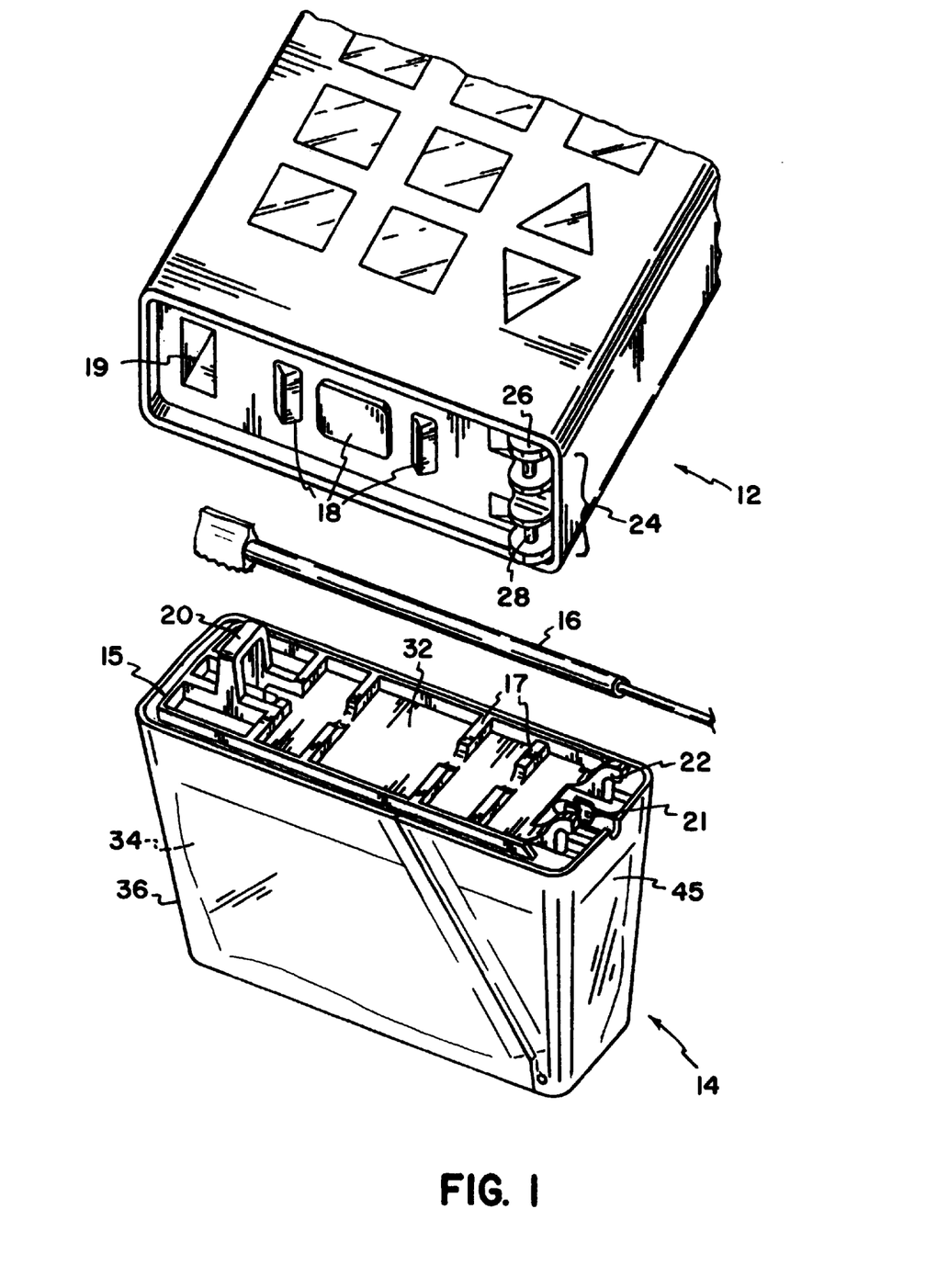
FIG. 1 is a perspective view of a first preferred embodiment of a system with a control module and a cassette of this invention.
Figure 2:
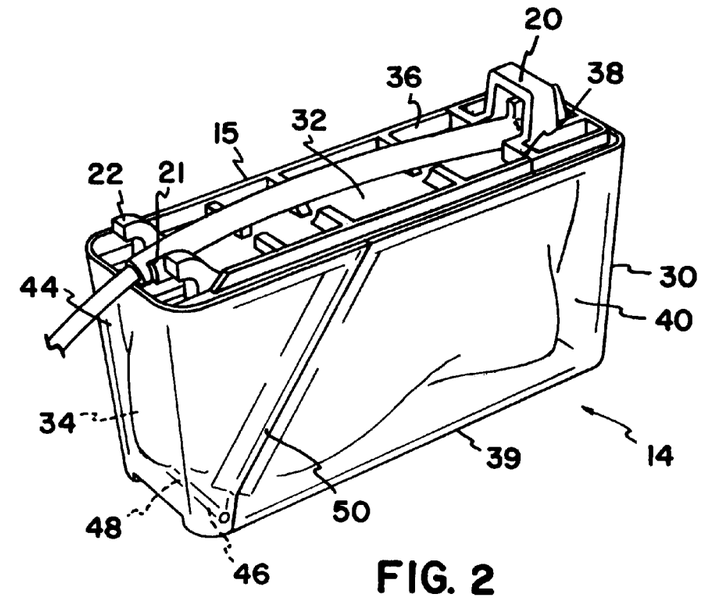
FIG. 2 is a further perspective view of the first preferred embodiment of a cassette of this invention.

Reference will now be made in detail to the present preferred embodiments of the invention wherein like numerals indicate like elements through the several views. FIG. 1 is a perspective view of one type of commonly-used ambulatory pump of this invention employing a linear peristaltic delivery mechanism. The ambulatory pump 10 of FIG. 1 comprises a control module 12 and a cassette 14. Cassette 14 (also shown in FIGS. 2 and 3) includes a pressure plate 15, a tubing support surface 32 and a housing 30 to enclose a fluid reservoir 34. Tubing support surface 32 includes a plurality of rib pairs 17 that serve as guides to position the tube in place along tubing support surface 32. Tube 16 passes between the control module 12 and cassette 14, between rib pairs 17 of tubing support surface 32 such that compressions from a plurality of tube-engaging members 18 on control module 12 sequentially compress tube 16 against pressure plate 15 to direct fluid through tube 16 to the patient.

In these types of infusion systems, cassette 14 is secured to control module 12 through the use of a pump anchor or loop 20. Pump anchor 20 engages a releasable securing mechanism inside control module 12 within cavity 19. Cassette 14 is also secured to control module 12 using at least one pump securing extension or hook 22. Cassette 14 includes two pump securing extensions 22. Pump securing extensions 22 engage a suspended pin assembly 24 on control module 12 having support structures 26 and pins 28. At least one clip 21 is positioned adjacent pump securing extensions 22 to hold tube 16 in place along tubing support surface 32.

Cassette 14 includes a housing 30 extending from pressure plate 15 and a tubing support surface 32. Cassette 14 houses a fluid reservoir 34 within housing 30. Fluid reservoir 34 can take any of a variety of shapes including a fluid-filled bag or a syringe.

Figure 3:
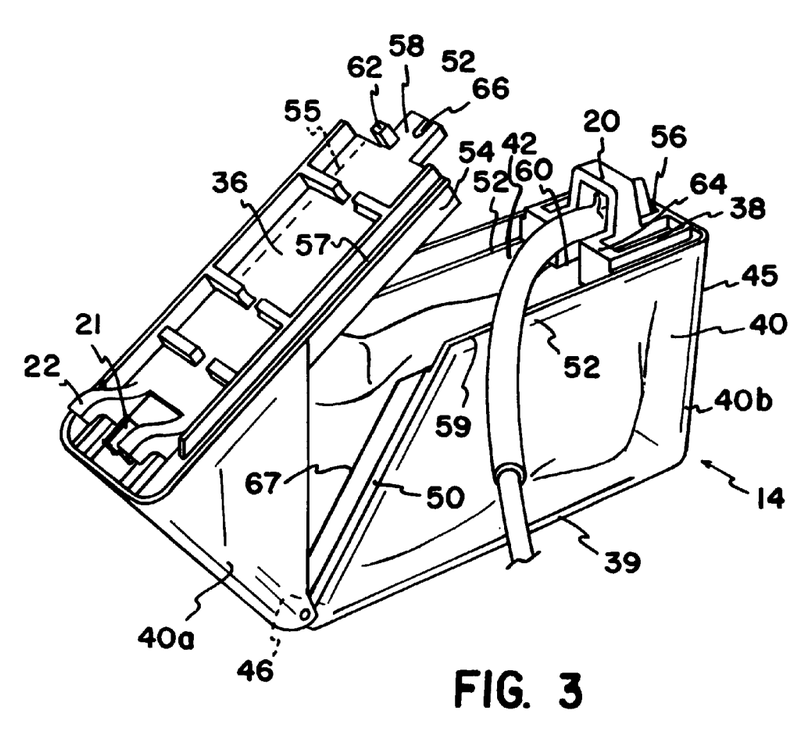
FIG. 3 is a perspective view of the preferred embodiment of FIG. 2 opened to remove or receive a fluid reservoir and tube.

In this embodiment, tubing support surface 32 is prepared as a first support surface portion 36 and a second support surface portion 38 (see FIG. 3). Housing 30 includes a bottom surface 39, and substantially planar sides including a front face 40, a back face 42 and two side faces 44 and 45.

In this embodiment, a hinge 46 is provided across one bottom corner of the device. In a preferred aspect of this embodiment, the hinge is formed as a pin 48 extending along one bottom corner of the housing from front face 40 to back face 42. Separation of first support surface portion 36 and second support surface portion 38 provides access to fluid reservoir 34. During separation, first tubing support surface portion 36, second tubing support surface portion 38, front face 40 and back face 42 separate along housing separation lines 50 positioned along front face 40 and back face 42. Hinge 46 defines an axis of rotation generally transverse to front face 40 and back face 42. Hinge 46 of can take any of a variety of forms and those skilled in the art will readily recognize that there are any number of hinged structures that could function equivalently in this embodiment.

First tubing support surface portion 36 extends along the tubing support surface 32, beyond housing separation lines 50, toward second tubing support surface portion 38. A support lip 52 (see FIG. 3) extends along the upper internal aspects of both front 40 and back face 42 and provides a shoulder to support first tubing support surface portion 36. A front support extension 54 and a back support extension 55 extend from the under surface on first tubing support surface portion 36 adjacent both front face 40 and back face 42, respectively. When first tubing support surface portion 36 and second tubing support surface portion 38 are aligned to form tubing support surface 32, support extensions 54, 55 rest along support lip 52. A side extension 57 of first tubing support surface portion 36 rests on a top edge 59 of front face 40 to provide for further secure engagement of the parts in the closed position. A tongue 58 extends from first tubing support surface portion 36 to mate with a groove 60 positioned on second tubing support surface portion 38. A snap or other lock can be provided to hold cassette 14 in the closed position.

A tubing port 56 is provided within second tubing support surface portion 38. Preferably this port 56 is positioned beneath anchor 20 and tube 16 extends from the port opening. In a preferred aspect of this embodiment, a first tubing guide 62 is positioned on tongue 58 and is paired on second tubing support surface portion 38 with a second tubing guide 64. A notch 66 is provided on tongue 58 to accommodate an edge of the fluid reservoir. Tongue 58 can be modified to accommodate a variety of fluid reservoirs. Groove 60 and port 56 form a continuous aperture to permit the addition and removal of fluid reservoir 34 from housing 30.

A needle guard 67 mounted to front face 40 of housing 30 overlaps the joint formed by the housing portions 40a, 40b making up front face 40. Needle guard 67 provides a secure joint region to eliminate needle access sites. A similar arrangement is provided on back face 42.

When cassette 14 is latched to control module 12, cassette 14 cannot be opened to access fluid reservoir 34. Control module 12 also preferably includes a lock to limit access to cassette 14 by preventing unauthorized unlatching.

To remove and replace a fluid reservoir, the securing mechanism (latch) within control module 12 is activated to release pump anchor 20 from within cavity 19. Pump securing extensions 22 on cassette 14 are disengaged from pin assembly 24. Tube 16 is removed from clip 21. First tubing support surface portion 36 is separated from second tubing support surface portion 38 and housing 30 is separated by splaying housing 30 using hinge 46 along housing separation lines 50 to access fluid reservoir 34. The fluid reservoir is removed by pulling reservoir 34 from housing 30 through tubing port 56 and through the opening created by the discontinuity of tubing support surface 32 when first tubing support surface portion 36 is separated from second tubing support surface portion 38.

Cassette 14 can be sterilized prior to reuse, if necessary, using either radiation or heat sterilization (where the housing is heat sterilization stable). Replacement tube 16 linked to a replacement fluid reservoir 34 is positioned through tubing port 56. The replacement reservoir is positioned within housing 30 and first tubing support surface portion 36 is realigned, adjacent second tubing support surface portion 38, through the rotation of first tubing support surface 36 around pin 48 toward second tubing support surface 38 to form continuous tubing support surface 32. Tube 16 is engaged with clip 21. Pump securing extensions 22 on tubing support surface 32 are engaged on pin assembly 24 and pump anchor 20 is introduced into cavity 19 of control module 12 to engage the releasable securing mechanism.

By splitting tubing support surface 32 downstream of anchor 20, potential problems with threading tube 16 through pressure plate 15 are avoided. Often tube 16 includes a fitting between the reservoir and the patient. Such a fitting may create problems if tube 16 must be threaded through a small opening in order to remove and replace the tube to reuse pressure plate 15. The two-piece construction of pressure plate 15 avoids the threading problem. Without this construction or another construction to allow access to tubing port 56, the fittings have to be detached from tube 16 during removal and replacement.

Figure 4:
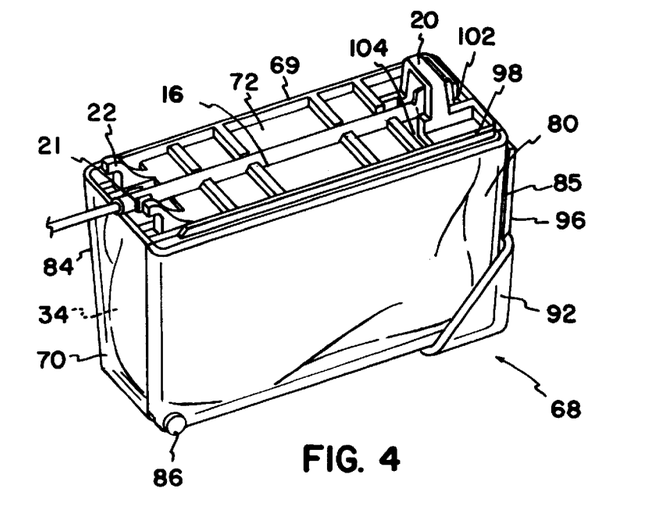
FIG. 4 is a perspective view of a second preferred embodiment of a cassette of this invention.
Figure 5:
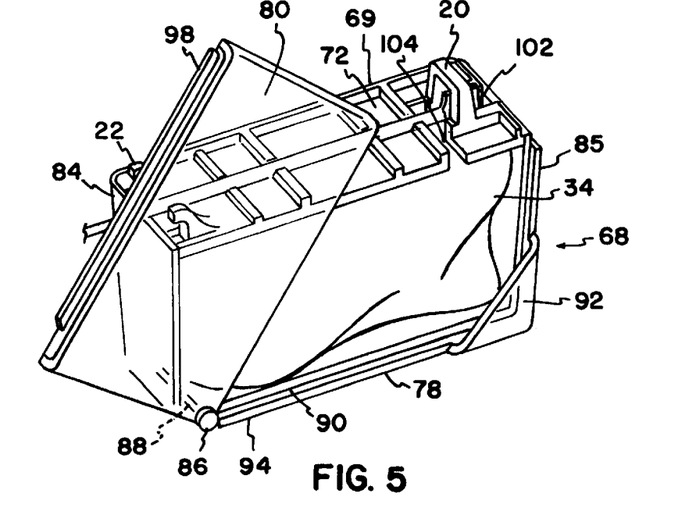
FIG. 5 is a perspective view of the preferred embodiment of FIG. 4 opened to remove or receive a fluid reservoir and tube.
Figure 6:
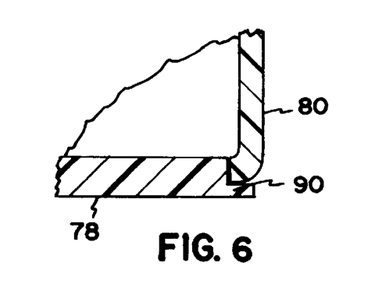
FIG. 6 is a cross-sectional view of a portion of the interface of the front face and the bottom surface of the second preferred embodiment of this invention.

FIGS. 4–6 provide a second preferred embodiment of a cassette 68. Cassette 68 includes a housing 74 and a pressure plate 69 having a continuous tubing support surface 72. Cassette housing 74 includes a bottom surface 78, substantially planar sides including a front face 80, a back face 82, an opposite front face 80, and two side faces 84 and 85. In this embodiment, a hinge 86 is provided at a bottom front corner of housing 74. Preferably, although not required, pressure plate 69 is permanently attached to back face 82 and side faces 84 and 85.

In a preferred aspect of this embodiment, hinge 86 is formed as a pin 88 that anchors front face 80 to the remaining portions of the housing and permits rotation of front face 80 relative to a remainder of housing 74 to provide access to fluid reservoir 34. A front face support 90 is provided as a shoulder extending from bottom 78 adjacent the lower aspect of front face 80 to support the lower aspect of the front face 80. A positioning support 92, with a bottom support plane 94 and a side support plane 96, is used to further align front face 80 onto cassette 68 to house reservoir 34. Front face support 90 forms part of bottom support plane 94, and bottom support plane 94 and side support plane 96 mount positioning support 92 to the housing 70. Positioning support 92 can be prepared as a separate piece to be affixed to the housing by adhesive, heating welding, or the like. Alternatively, the front face support can be molded together with the housing. Positioning support 92 prevents front face 80 from being pried open when cassette 68 is in the closed position.

In FIGS. 4 and 5, hinge 86 is positioned at a first bottom corner of front face 80 beneath pump securing extensions 22, and positioning support 92 is positioned over a second bottom corner of front face 80. When front face 80 is positioned to enclose fluid reservoir 34, front face support 90 supports the lower aspects of the front face 80 as shown in FIG. 6. Hinge 86 defines an axis of rotation generally transverse to rotatable front face 80.

The top edge of front face 80 includes a ridge 98. The ridge serves to further secure cassette 68 to control module 12 when pump securing extensions 22 and pump anchor 20 are engaged on the control module. It is possible to provide a snap fit or other lock to restrict movement between front face 80 and housing 70 when front face 80 is closed to restrict access to fluid reservoir 34 and is positioned adjacent to front face support 90. Like hinge 46 of FIGS. 1–3, hinge 86 shown in FIGS. 4 and 5 can take any of a variety of forms and those skilled in the art will readily recognize that there are any number of hinged structures that could function equivalently in this embodiment, including those variations discussed in association with FIGS. 1–3.

A tubing port 102 is provided under pump anchor 20 to permit a tube to extend from the internal portion of the housing 70 to tubing support surface 72. A slot 104 communicates with port 102 to facilitate assembly and disassembly of tube 16 with respect to cassette 68 when fluid reservoir 34 is added or removed from housing 70.

To remove and replace a fluid reservoir 34 from cassette 68, the securing mechanism within control module 12 is activated to release pump anchor 20 from within control module cavity 19 (see FIG. 1). Pump securing extensions 22 on cassette 68 are disengaged from pin assembly 24. Cassette 68 is now separable from control module 12. In the embodiment of FIGS. 4–6, front face 80 is rotated counterclockwise around hinge mechanism 86 to provide access to fluid reservoir 34. Fluid reservoir 34 is removed through the opening created by rotation of front face 80. Fluid reservoir 34 is separated from housing 70 and tube 16 is positioned in tubing port 102. Tube 16 is also separated from clip 21.

Cassette 68 can be sterilized prior to reuse, if necessary, using either radiation or heat sterilization (where the housing is heat sterilization stable). Tube 16, linked to a replacement fluid reservoir, is positioned in housing 70 and the tube is extended through tubing port 102. Front face 80 is rotated clockwise to realign front face 80 with back face 82 and to position front face 80 adjacent to the internal surface of positioning support 92. Tube 16 is engaged with clip 21. Pump securing extensions 22 on tubing support surface 72 are engaged on pin assembly 24 on control module 12 and pump anchor 20 is introduced into cavity 19 to engage the releasable securing mechanism within control module 12 (see pump shown in FIG. 1).

The hinged face 80 and slot 104 allow for tube 16 to be removed and replaced with a new tubing without problems arising due to any large fittings downstream on tube 16 interfering with pressure plate 69. When cassette 68 is latched to control module 14, front face 80 cannot be moved from its closed position, thereby limiting access to fluid reservoir 34.

Figure 8:
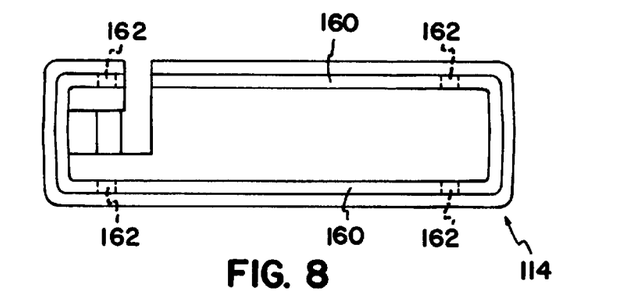
FIG. 8 is a bottom view of the pressure plate of the embodiment of FIG. 7.
Figure 9:
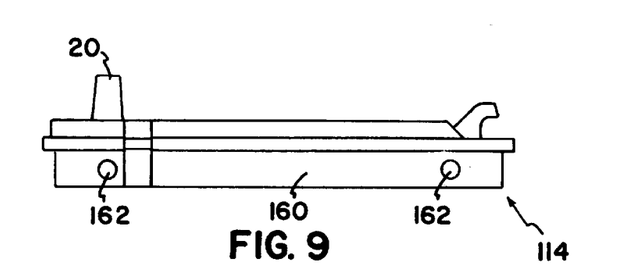
FIG. 9 is a side view of the pressure plate of the embodiment of FIG. 8.
Figures 10, 11, 12:
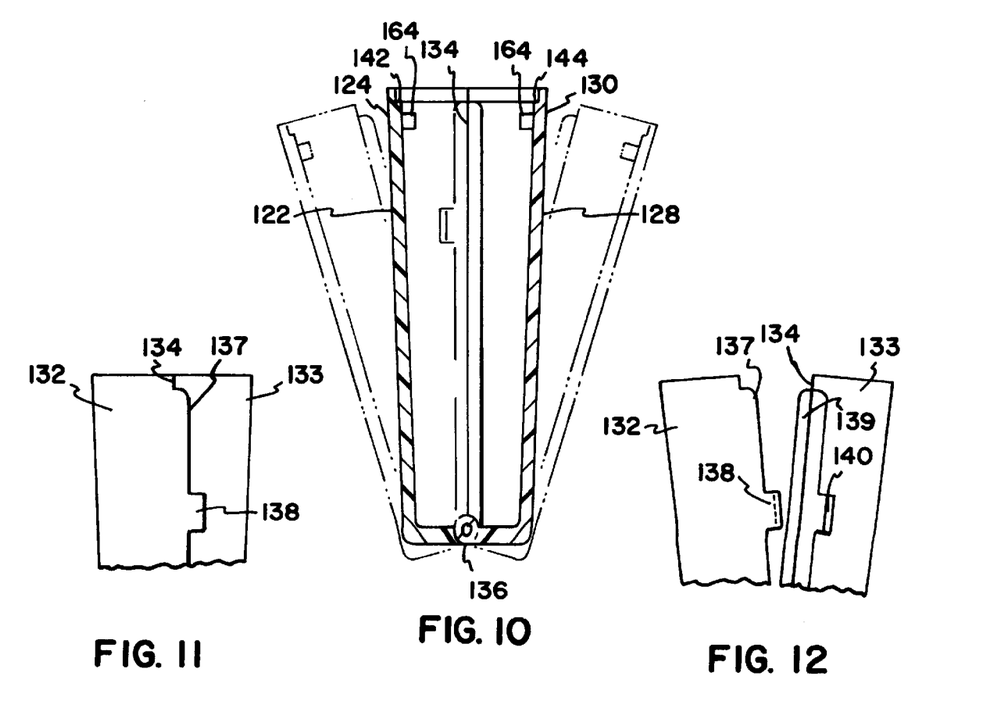
FIG. 10 is a cross-sectional end view of the housing of the embodiment of FIG. 7.
FIG. 11 is an end view of a preferred closing mechanism, in the closed position, for the embodiment of FIG. 7.
FIG. 12 is an end view of the preferred closing mechanism, in the open position, for the embodiment of FIG. 7.

FIGS. 7–12 show a third preferred embodiment of this invention. In this embodiment a cassette 110 is prepared as a housing 112 and a pressure plate 114. Housing 112 separates along sides 116 and 118 and bottom 120 to separate housing 112 into a front half 122 having a front face 124 and front side portions 126 and 127, and a back half 128 having a back face 130 and back side portions 132 and 133 along separation line 134 as illustrated in FIG. 10. Separation line 134 extends continuously along side 116, bottom 120 and side 118. A hinge 136 mounted along bottom 120 is preferably prepared as a pin assembly extending from side 116 to side 118. Hinge 136 defines an axis of rotation generally parallel to tube 16. FIG. 10 provides a cross sectional end view of housing 112 with hinge 136.

At least one extending grip 138 is provided along at least one side of housing 112. Extending grips 138 extend across front half 122 and back half 128 of front side portions 126 and 127 and at least one receiving grip 140 is positioned to receive matched extending grip 138. Extending grips 138 and receiving grips 140 are preferably mounted on each side of housing 112. FIG. 11 shows extending grip 138 and receiving grip 140 in a closed position while FIG. 12 shows extending grip 138 and receiving grip 140 in an open position. Grips 138 and 140 function as a releasable snap. Needle guards 137, 139 overlap to limit needle access sites into cassette 110. Other snaps and locks are anticipated to hold housing 112 in the closed position.

Figures 7, 13, 15:
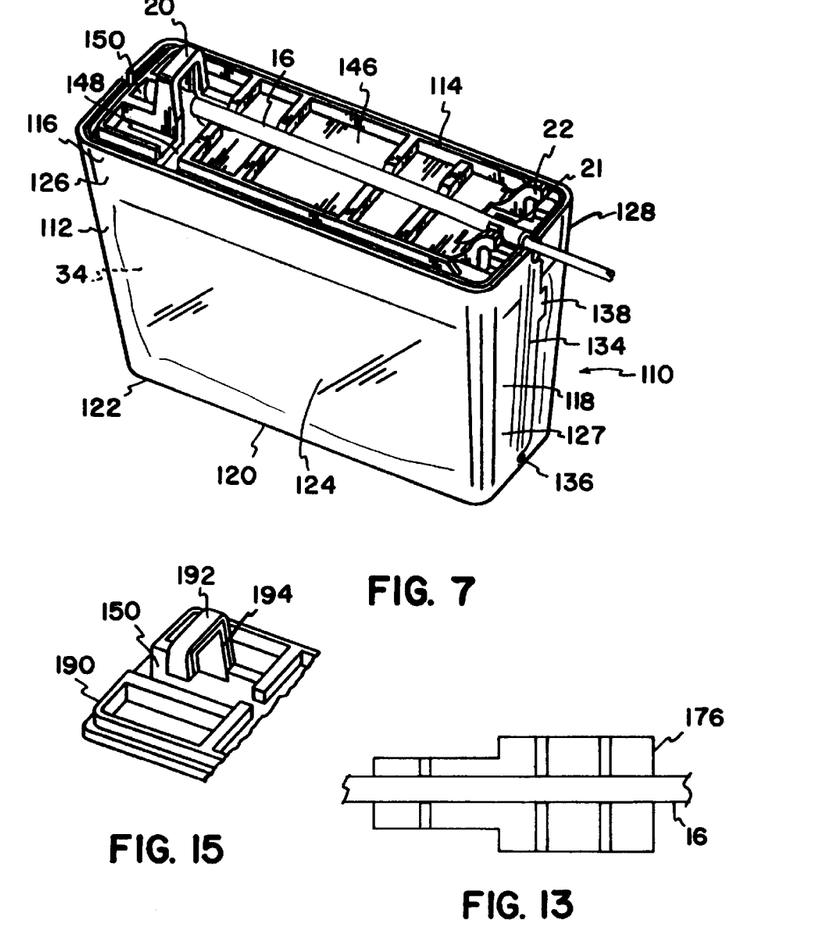
FIG. 7 is a perspective view of a third preferred embodiment of a cassette of this invention.
FIG. 13 is a top view of a fourth preferred embodiment of a pressure plate insert.
FIG. 15 is a fifth preferred embodiment of a pressure plate having an alternative anchor.
Figure 14:
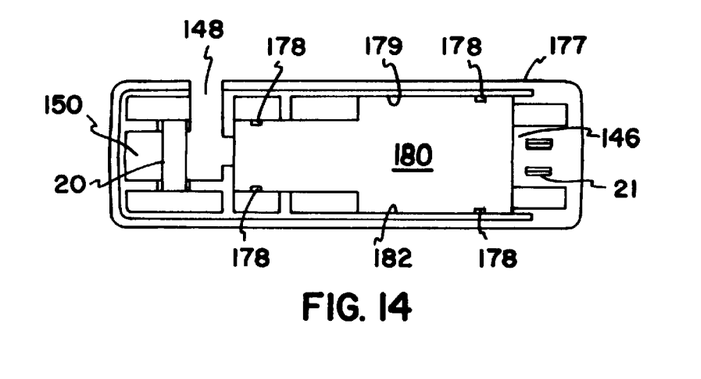
FIG. 14 is a top view of a preferred pressure plate for use with the insert of FIG. 13.

Pressure plate 114 is shown in side view in FIG. 9, by bottom view in FIG. 8 and by top view in FIGS. 7 and 14. Pressure plate 114 is removably mounted along a first support lip 142 of front half 122 and a second support lip 144 of back half 128. Pressure plate 114 includes a tubing support surface 146, anchor 20, rib pairs 17, at least one pump securing extension 22 and clip 21 (see FIG. 7). Port 150 positioned beneath anchor 20 is adapted to receive tube 16. Slot 148 and extends from the mid-portion of tubing support surface 146 and is continuous with port 150 to a lateral edge of tubing support surface 146. Slot 148 is provided as an access to assemble and disassemble tube 16 extending from fluid reservoir 34.

Referring now to FIG. 9, pressure plate 114 has a lip extension 160 extending around the circumference of the lower aspect of pressure plate 114. Lip extension holes 162 are positioned along the lateral aspects of lip extension 160. Lip extension posts or pins 164 (see FIG. 10) extend from the upper aspect of front face 124 and the upper aspect of back face 130. Lip extension pins 164 are positioned to be receivably inserted into lip extension holes 162. Holes 162 and pins 164 cooperate to retain pressure plate 114 with housing 112 in the closed position.

For cassette 110, pressure plate 114 is disposable with tube 16 and reservoir 34, or reusable, as desired. In the case of a reusable cassette, pressure plate 114 can be permanently mounted to back half 128 of housing 112. Adhesive or an ultrasonic weld at second support lip 144 would permanently mount the pressure plate to the back half. Slot 148 is useful for tube removal and new tube attachment when pressure plate 114 is reused. Slot 148 eliminates the need for tube 16 to be threaded through post 150. Such threading could be time consuming and difficult since tube 16 may have a fitting or other large structure downstream from the pressure plate that would otherwise have to be removed during removal of the tube. If pressure plate 114 is disposable, slot 148 is optional. Tube 16 can be permanently mounted to pressure plate 114. Clip 21 can be replaced by a closed loop, if desired. If access to an interior of cassette 110 is a concern, retaining portions can extend from either or both of cassette 110 and control module 14 so that when cassette 110 is mounted to control module 14, portions of cassette 110 and control module 14 engage one another so that front and back halves 122, 128 of housing 112 cannot be pivoted apart. The retaining portions would trap housing 112 in the closed position to further limit access to fluid reservoir 34. Alternatively, more secure snaps or locks can be used to hold cassette 110 closed.

The embodiments noted above involve reusable pressure plates and housings (FIGS. 1, 4, and 7) and reusable housings with disposable pressure plates (FIG. 7). In some applications, it may be desirable to reuse a portion of the pressure plate. FIGS. 13–15 show details of embodiments where a portion of the pressure plate is reused (hooks and loop), while a portion is disposed of with the used tube. FIGS. 13 and 14 show a two-piece pressure plate construction wherein a reusable pressure plate 177 receives a disposable insert 176.

As shown in FIGS. 13 and 14, tubing support surface 146 of pressure plate 177 is adapted to receive separate insert 176. Insert tabs 178 on pressure plate 14 secure insert 176 in place on tubing support surface 146. Insert 176 fits into recess 179 on tubing support surface 146. Tube 16 can be glued or otherwise permanently attached to insert 176, as desired. Tube 16 and insert 176 can be discarded after use, while pressure plate 114 is reused. FIG. 14 illustrates slot 148 on an opposite side of pressure plate 177 from that shown in FIG. 7.

When pressure plate 177 is mounted to control module 14, insert 176 is trapped securely between a recessed top surface 180 of pressure plate 177 and control module 14. An edge 182 of recess 179 keeps insert 176 from moving laterally when pressure plate 177 is mounted to control module 14. The tube engaging members of control module 14 squeeze tube 16 against insert 176. When pressure plate 177 is separated from control module 14, insert tabs 178 releasably grip separate insert 176 to retain the insert with pressure plate 177 for handling as a single unit. Pressure plate 177 can be mounted to a housing similar to housing 112 to enclose a fluid reservoir. Alternatively, pressure plate 177 can be mounted to a control module 14 for use with a remote reservoir. In such a case, it may be desirable to slot anchor 20 to allow ease of removal and replacement of tube 16 and insert 176.

FIG. 15 shows an alternative pressure plate 190 with a slotted anchor 192 configured as a hook. Port 150 is positioned beneath anchor 192. Pressure plate 190 is made of a durable material. If desired, anchor 192 can be reinforced using a metal reinforcement 194 if the rest of plate 190 is made of molded plastic. Anchor 192 provides ready access to assemble and disassemble tube 16 through port 150, such as in the case of needing to position the tube under anchor 192 without having to thread the tubing through a small opening. Also, hooks 22 can be reinforced if desired. The embodiment of FIG. 15 is useful with remote fluid reservoirs.

When the pressure plate or a portion of the pressure plate is reusable, suitable materials for its construction are desired so as to ensure proper mounting to the pump and proper fluid delivery. The material or materials selected should withstand repeated reuses with the pump a suitable number of times and also allow the pump to pump properly without free flow or without requiring excessive energy drain and/or causing a stoppage of the pumping mechanism. All metal, molded plastic with metal reinforcement, and glass-filled plastic are possible constructions for a reusable pressure plate.

Although characteristics and advantages, together with details for structure, materials, function and process steps, have been described in reference to preferred embodiments herein, it is understood that the disclosure is illustrative. To that degree, various changes made especially to matters of shape, size and arrangement to the full extent extended by the general meaning of the terms in which the appended claims are expressed, are within the principles of the present invention.

What is claimed is:

1. A cassette mountable to a pumping mechanism for positioning a tube adjacent to a plurality of tube engaging members of the pumping mechanism, the cassette comprising:

a housing sized to hold a fluid reservoir, the housing having a bottom face, a front face, a back face and two side faces;

a pressure plate mountable to the housing and having an anchor and two hooks, the pressure plate having a tubing support surface;

a hinge extending along the bottom face of the housing to separate the housing into a front half and a back half to reversibly open and close the housing to access an interior of the housing;

a snap to hold the front half to the back half in a closed position; and means for retaining the pressure plate with the front half and the back half of the housing in the closed position.

2. The cassette of claim 1, wherein the means for retaining includes a post and hole arrangement between the housing and the pressure plate.

3. The cassette of claim 1, wherein the means for retaining includes a permanent mount between the back half and the pressure plate.

4. The cassette of claim 3, wherein the pressure plate includes a slot extending to an edge adjacent the front half, the slot sized to receive the tube.

5. The cassette of claim 1, wherein the pressure plate includes a slot extending to an edge adjacent the front half.

6. The cassette of claim 1, wherein the front half and the back half overlap at a junction between the two halves.

7. A method for using a cassette for positioning a tube adjacent to a pumping mechanism, the method comprising the steps of:

providing a cassette having a housing with a bottom face, a front face, a back face, and two side faces, a hinge extending across the bottom face and a tubing support surface;

opening the housing along the hinge to separate the housing along a housing separation line extending along the side faces to separate the housing into a front half and a back half;

positioning a fluid reservoir and a tube within an interior of the housing;

extending the tube along the tubing support surface of the housing;

closing the housing;

snapping the housing in the closed position; and mounting the cassette to the pumping mechanism.

8. The method of claim 7, further comprising the step of inserting the tube into a slot formed in an edge of the tubing support surface.

9. The method of claim 7, further comprising the steps of:

separating the cassette from the pumping mechanism;

opening the housing to access the interior of the housing;

removing the fluid reservoir and tube from the housing;

positioning a second fluid reservoir and a second tube within the housing;

extending the second tube along the tubing support surface of the housing;

closing the housing;

snapping the housing in the closed position; and mounting the cassette with the second fluid reservoir and the second tube to the pumping mechanism.

* * * * *